United States Patent
Woo

(10) Patent No.: US 6,706,285 B1
(45) Date of Patent: Mar. 16, 2004

(54) ENTERIC COATED FORMULATION OF A BENZIMIDAZOLE DERIVATIVE AND METHOD FOR PREPARATION THEREOF

(75) Inventor: Jong Soo Woo, Suwon-shi (KR)

(73) Assignee: Hanms Pharm. Co., Ltd., Kyunggi-do (KR)

( * ) Notice: Subject to any disclaimer, the term of this patent is extended or adjusted under 35 U.S.C. 154(b) by 0 days.

(21) Appl. No.: 09/357,570

(22) Filed: Jul. 20, 1999

(30) Foreign Application Priority Data

Oct. 1, 1998 (KR) ............................... 98-41349

(51) Int. Cl.$^7$ .............. A61K 9/14; A61K 9/28; A61K 9/20; A61K 31/415
(52) U.S. Cl. ............... 424/483; 424/464; 424/474; 424/485; 424/484; 514/394
(58) Field of Search ................ 424/474, 485, 424/483, 464, 484; 514/394

(56) References Cited

U.S. PATENT DOCUMENTS 4,147,768 A * 4/1979 Shaffer et al.

FOREIGN PATENT DOCUMENTS

KR 135736 4/1989

OTHER PUBLICATIONS

Pilbrant, A. and Cederberg C., "Development of an oral formulation of omeprazole", Scand. J. Gastoenterology 1985, 20 (Suppl. 180), pp. 113–120.

G. Rackur, et al., "2–((2–Pyridylmethyl) Sulfinyl) Benzimidazole: Acid Sensitive Suicide Inhibitors of the Proton Transport System in the Parietal Cell", Biochemical Biophysical Research Comm., 1985, 128(1) p. 477–484.

* cited by examiner

Primary Examiner—Thurman K. Page
Assistant Examiner—Amy E Pulliam
(74) Attorney, Agent, or Firm—Sherman & Shalloway

(57) ABSTRACT

Disclosed are an enteric coated formulation of a benzimidazole derivative comprising a core and a film of an enteric coating agent on the surface thereof, the core containing a complex of the benzimidazole derivative and an ion-exchange resin, and the enteric coating agent having the degree of substitution by an acidic group of less than 30%, and a method for preparation thereof.

2 Claims, No Drawings

ENTERIC COATED FORMULATION OF A BENZIMIDAZOLE DERIVATIVE AND METHOD FOR PREPARATION THEREOF

TECHNICAL FIELD

The present invention relates to an enteric coated formulation of a benzimidazole derivative and a method for preparation thereof. More specifically, the present invention relates to the enteric coated formulation of the benzimidazole derivative comprising a core and a film of an enteric coating agent on the surface thereof, the core containing a complex of the benzimidazole derivative and an ion-exchange resin, and the enteric coating agent having the degree of substitution by an acidic group of less than 30%, and the method for preparation thereof.

BACKGROUND ART

Benzimidazole derivatives have the basic skeletal structure of the following formula 1:

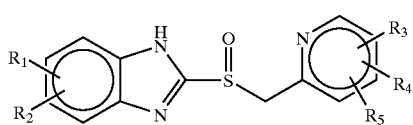

Formula 1

Representative examples of the benzimidazole derivatives are omeprazole, pantoprazole, lansoprazole, timoprazole, and picoprazole, etc., and many kinds of compounds further exist. Among the above-described compounds, Omeprazole(5-methoxy-2[[(4-methoxy-3,5-dimethyl-2-pyridinyl)methyl]sulfinyl]-1H-benzimidazole) has the structure as represented by the following formula 2:

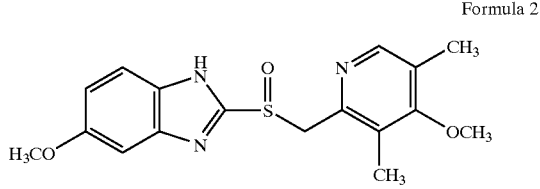

Formula 2

Pantoprazole(5-difluoromethoxy-2[[(3,4-dimethoxy-2-pyridinyl)methyl]sulfinyl]-1H-benzimidazole) has the structure as represented by the following formula 3:

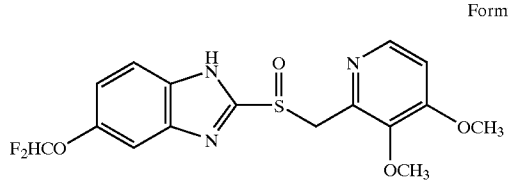

Formula 3

Lansoprazole(2-[[[3-methyl-4-(2,2,2-trifluoroethoxy)-2-pyridinyl]meth yl]sulfinyl]-1H-benzimidazole) has the structure as represented by the following formula 4:

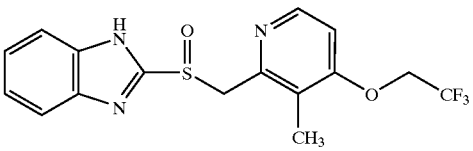

Formula 4

Timoprazole(2-[[(2-pyridinyl)methyl]sulfinyl]-1H-benzimidazole) has the structure as represented by the following formula 5:

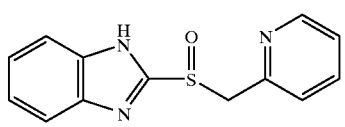

Formula 5

Picoprazole(5-ethoxycarbonyl-6-methyl-2[[(3-methyl-2-pyridinyl)meth yl]sulfinyl]-1H-benzimidazole) has the structure as represented by the following formula 6:

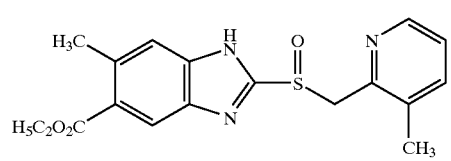

Formula 6

Among the above-described benzimidazole derivatives, particularly, omeprazole suppresses strongly the secretion of acid in the stomach, and thus, is clinically very useful for the treatment of gastric or duodenal ulcer. However, it is extremely unstable under the acidic or neutral condition, and thus, is severely restricted in its formulation.

In particular, omeprazole has a half-life of less than 10 minutes under the acidic condition at a pH of 4 or less. Moreover, the product formed by degradation is also acidic, and thus, under the acidic condition, degradation of omeprazole is rapidly accelerated with the lapse of time. In contrast, the half-life of omeprazole is prolonged to about 14 hours under the neutral condition at a pH of about 7.0. As a pH becomes higher, its half-life becomes longer. It has been reported that its half-life is about 300 days at a pH of 11(Pilbrant and Cederberg, Scand. J. Gastroenterology, 1985, 20 (Suppl. 108), p113–120). Degradation of omeprazole is known as an acid-catalyzed rearrangement reaction (G. Rackur et al., Biochem, Biophys, Res. Commun. 1985; 128(1), p466–484).

Accordingly, in the case of an orally administrable formulation of a benzirnidazole derivative, the benzimidazole derivative is not allowed to be exposed to acidic gastric juice in order not to be degraded in the stomach and to reach the intestine. In particular, in the case of omeprazole, an alkaline ingredient must be contained as a stabilizing agent in a core containing omeprazole in order to improve its storage stability. Therefore, the literature [Pilbrant and Cederberg, Scand. J. Gastroenterology, 1985, 20 (Suppl. 108), p113–120] disclosed an enteric coated formulation of omeprazole, the core of which contains the alkaline ingredient and is coated with an enteric coating agent. However, since a conventional enteric coating agent has the high degree of substitution by an acidic group in order to increase acid-stability of an active ingredient, they may have undesirable effects on stability of the benzimidazole derivative. In addition, the enteric coating film of the formulation may be impaired by the alkaline ingredient as the stabilizing agent and thus, the formulation has problems that its storage stability is unsatisfactory in the long term.

Various approaches have been developed in order to solve the problems involved in formulation of a benzimidazole derivative due to its stability. For example, the Korean patent publication No. 91-4579 disclosed a method for preparing an enteric coated formulation of omeprazole using an inorganic alkalinizing agent as a stabilizing agent of omeprazole. The above-described method comprises the steps of forming a core containing omeprazole and the inorganic alkalinizing agent, forming a water-soluble inner film on the surface of the core, and subsequently forming an enteric coating film on the surface of the inner film. However, the method is very complicated because it involves the coating process consisting of two steps. In addition, if the water-soluble inner film is not or incompletely formed, the enteric coating film interacts with the alkaline core, and thus, its storage stability is severely decreased.

In order to solve the above-mentioned problems, the present inventors have repeated the extensive studies to improve the stability of a benzimidazole derivative without using an alkalinizing agent. As a result, the present inventors developed a complex of omeprazole and an ion-exchange resin which can be formulated into various dosage forms(the Korean patent No. 135736, Jan. 16, 1998). The complex has the advantage of exhibiting excellent stability in comparison with omeprazole or salts thereof as such. In the specification of the patent, it has been already described that an enteric coating film may be directly formed on the surface of the complex without forming a water-soluble inner film. However, if the water-soluble inner film is not formed on the surface thereof, even the complex still has problems that its storage stability is not satisfactory since an acidic group of the enteric coating agent has undesirable effects on the complex.

DISCLOSURE OF THE INVENTION

Accordingly, in order to solve the problems involved in the above-mentioned prior arts, an object of the present invention is to provide an enteric coated formulation of a benzimidazole derivative not only exhibiting excellent acid-stability and storage stability without a water-soluble inner film but also being rapidly disintegrated and dissolved at the absorption sites.

Another object of the present invention is to provide a method which makes it possible to simply prepare an enteric coated formulation of a benzimidazole derivative exhibiting excellent acid-stability and storage stability by omitting the step of forming a water-soluble inner film on the surface of a core.

The present invention provides an enteric coated formulation of a benzimidazole derivative comprising a core and a film of an enteric coating agent on the surface thereof, the core containing a complex of the benzimidazole derivative and an ion-exchange resin, and the enteric coating agent having the degree of substitution by an acidic group of less than 30%. The benzimidazole derivative includes, but is not limited to, omeprazole, lansoprazole, pantoprazole, timoprazole or picoprazole. In a preferable embodiment, the ion-exchange resin is an anion-exchange resin, and in a more preferable embodiment, cholestyramine resin or Dowex resin. In a preferable embodiment, the enteric coating agent has the degree of substitution by the acidic group of 27% or less. In particular, it is hydroxypropyl methylcellulose phthalate. In the most preferable embodiment, it is hydroxypropyl methylcellulose phthalate having the degree of substitution by phthalic acid of 20 to 27%.

The present invention also provides a method for preparation of an enteric coated formulation of a benzimidazole derivative, comprising the step of coating a core containing a complex of a benzimidazole derivative and an ion-exchange resin with an enteric coating agent having the degree of substitution by an acidic group of less than 30%.

BEST MODE FOR CARRYING OUT THE INVENTION

Hereinafter, the present invention will be more specifically explained. According to the present invention, a complex of a benzimidazole derivative and an ion-exchange resin is used instead of the benzimidazole derivative or salts thereof as such. The complex is prepared by dissolving the benzimidazole derivative in an aqueous alkaline solution and subsequently adding a separately activated ion-exchange resin thereto to form ionic bonds between the benzimidazole derivative and the ion-exchange resin, as disclosed in the Korean patent No. 135736, the content of which is incorporated hereinto by reference.

Either a cation- or an anion-exchange resin may be used as the ion-exchange resin. However, in the case of using the cation-exchange resin, since the reaction must be performed under the acidic condition to bind the benzimidazole derivative with the cation-exchange resin, there is a possibility that the benzimidazole derivative is degraded to decrease reaction yield. Therefore, it is preferable to use the anion-exchange resin and more preferable to use cholestyramine resin or Dowex resin such as cholestyramine(Duolite® AP-143), Dowex 1×2–400, Dowex 1×4–400, Dowex 1×8–400 or Dowex 1×8–50. For example, in the case of using cholestyramine resin, the complex of the benzimidazole derivative and cholestyramine resin has the structure as represented by the following formula 7:

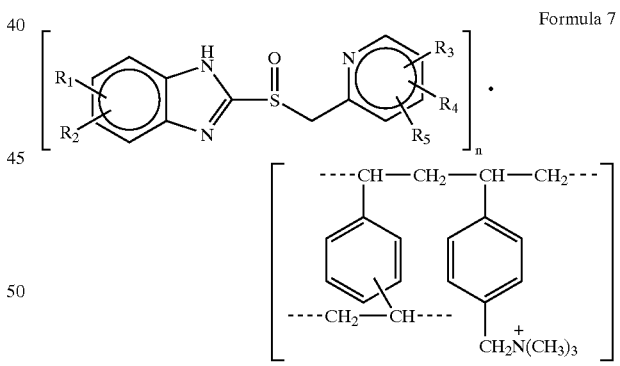

Formula 7

In the pharmaceutical field, a compound having the degree of substitution by an acidic group of 30% or more is conventionally used as an enteric coating agent in order to increase acid-stability of an active ingredient. For example, among hydroxypropyl methylcellulose phthalates, HPMCP® HP-55 is used which has the degree of substitution by phthalic acid of about 30~35% and among methacrylic acid/methacrylic acid methyl ester copolymers, Eudragit® L-100 is used which has the degree of substitution by methacrylic acid of 45~50%. However, when these conventional enteric coating agents are coated on an alkaline core, the formulation exhibits good acid-stability at first but its stability is gradually decreased in the long term.

Accordingly, in the present invention, a core containing a complex of a benzimidazole derivative and an ion-exchange resin is coated with an enteric coating agent having the low degree of substitution by an acidic group on the surface thereof to prepare an enteric coated formulation of the benzimidazole derivative. That is, an agent having the degree of substitution by the acidic group of less than 30%, preferably 27% or less is used as the enteric coating agent instead of the conventional enteric coating agent having the degree of substitution by the acidic group of 30% or more. For example, hydroxypropyl methylcellulose phthalate having the degree of substitution by phthalic acid of less than 30%, more preferably 27% or less, most preferably 20~27%, such as HPMCP® HP-50 is used. In this case, even if the core containing the complex of the benzimidazole derivative and the ion-exchange resin is directly coated with the enteric coating agent without a water-soluble inner film, since the enteric coating agent has the low degree of substitution by the acidic group, storage stability of the benzimidazole derivative can be ensured. Additionally, the formulation can be simply prepared by omitting the step of forming the water-soluble inner film. Furthermore, while the conventional enteric coating agent dissolves at a pH of 5.5 or more, the enteric coating agent having the low degree of substitution by the acidic group according to the present invention dissolves at a low pH, i.e. a pH of about 5.0 and thus, the benzimidazole derivative can be rapidly disintegrated and dissolved at the absorption sites.

EXAMPLES

This invention will be better understood from the following examples. However, one skilled in the art will readily appreciate the specific materials and results described are merely illustrative of, and are not intended to, nor should be intended to, limit the invention as described more fully in the claims which follow thereafter.

Examples 1~3

A composition for tablet cores which has the ingredients as shown in the following table 1 was uniformly mixed. The mixture was made into tablets by direct method to obtain tablet cores.

TABLE 1

Composition for tablet cores

| Ingredients (mg) | Example 1 | Example 2 | Example 3 |
|---|---|---|---|
| lansoprazole-cholestyramine complex | 40 | — | — |
| omeprazole-cholestyramine complex | — | 40 | — |
| pantoprazole-cholestyramine complex | — | — | 40 |
| hydroxypropyl cellulose-L | 45 | 45 | 45 |
| Lactose for direct method (Ludipress ®, BASF) | 193 | 193 | 193 |
| sodium starch glycolate | 21.2 | 21.2 | 21.2 |
| silicon dioxide | 0.8 | 0.8 | 0.8 |
| magnesium stearate | 2 | 2 | 2 |
| the total weight | 302 | 302 | 302 |

According to a conventional method for coating tablets, the obtained tablet cores were coated in a pan with a coating composition which has the ingredients as shown in the following table 2.

TABLE 2

Coating composition

| Ingredients | amount (mg) |
|---|---|
| Hydroxypropyl methylcellulose phthalate HP-50 | 40 |
| myvacet | 2 |
| acetone | 360 |
| 95% ethanol | 180 |

Examples 4~7

A composition for pellet cores which has the ingredients as shown in the following table 3 was uniformly mixed. Then, a suitable amount of binding solution(water:ethanol= 7:3) was added thereto.

It was made into pellets by wet method to obtain pellet cores.

TABLE 3

Composition for pellet cores

| Ingredients (mg) | Example 4 | Example 5 | Example 6 |
|---|---|---|---|
| lansoprazole-cholestyramine complex | 40 | — | — |
| omeprazole-cholestyramine complex | — | 40 | — |
| pantoprazole-cholestyramine complex | — | — | 40 |
| polyethylene glycol 6000 | 5.25 | 5.25 | 5.25 |
| D-sorbitol | 26.25 | 26.25 | 26.25 |
| microcrystalline cellulose | 50.75 | 50.75 | 50.75 |
| anhydrous lactose | 140 | 140 | 140 |
| polyvinylpyrrolidone K-30 | 1.75 | 1.75 | 1.75 |
| sodium starch glycolate | 52.5 | 52.5 | 52.5 |
| magnesium stearate | 3.5 | 3.5 | 3.5 |
| the total weight | 320 | 320 | 320 |

According to a conventional method for coating pellets, the obtained pellet cores were coated in a pan with a coating composition which has the ingredients as shown in above table 2.

Comparative Examples 1~6

The procedures were carried out in the substantially same manners as Examples 1~6, except that hydroxypropyl methylcellulose phthalate HP-55 was used instead of hydroxypropyl methylcellulose phthalate HP-50 among the ingredients of the coating composition.

Test Example 1

The coated tablets obtained from Examples 1~3 and Comparative Examples 1~3 were maintained in the open form under the accelerated condition(40° C. relative humidity of 75%) and change of their appearances was observed with the lapse of time. At that time, as a control formulation, the tablet "Rosec®" (by Yuhan, Corporation, Korea) was used which contains omeprazole as an active ingredient and $Na_2HPO_4$ as an alkaline stabilizing agent and is coated by double-coating method to form a water-soluble inner film and an enteric coating film.

The results are shown in the following table 4.

TABLE 4

Change of appearances

|  | At first | After 7 days | After 14 days |
| --- | --- | --- | --- |
| Example 1 | pale yellow | pale yellow | pale yellow |
| Example 2 | pale yellow | pale yellow | pale yellow |
| Example 3 | pale yellow | pale yellow | pale yellow |
| Comparative Example 1 | brownish white | brownish white | brown |
| Comparative Example 2 | brownish white | brownish white | brown |
| Comparative Example 3 | brownish white | brownish white | brown |
| Control formulation | pale yellow | brown | deep brown |

The above table 4 shows that the formulations according to the present invention have excellent storage stability without change of appearances with the lapse of time.

Test Example 2

In Test Example 1, change of the contents of a benzimidazole derivative with the lapse of time was measured by liquid chromatography method.

Column; μ-Bondapak® $C_{18}$

Detection; UV 280 nm

Mobile phase; acetonitrile: phosphate buffer at a pH of 7.6=34:66

Injection volume; 10 μl

Flow rate; 1.1 ml/min

The results are shown in the following table 5.

TABLE 5

Content of the benzimidazole derivative (%)

|  | At first | After 7 days | After 14 days |
| --- | --- | --- | --- |
| Example 1 | 100 | 100 | 98 |
| Example 2 | 101 | 100 | 98 |
| Example 3 | 100 | 99 | 97 |
| Comparative Example 1 | 98 | 95 | 91 |
| Comparative Example 2 | 99 | 96 | 90 |
| Comparative Example 3 | 99 | 97 | 89 |
| Control formulation | 98 | 88 | 74 |

As shown in the above table 5, after 14 days, the content of the benzimidazole derivative was decreased to 89~91% in the coated tablets according to Comparative Examples 1~3 and to 74% in the control formulation, respectively. In contrast, the coated tablets according to Examples 1~3 maintained the content of the benzimidazole derivative of 97% or more and thus, it was identified that the coated tablets of the present invention have excellent long-term storage stability.

Accordingly, the formulation according to the present invention has excellent acid-stability and storage stability, and can be rapidly disintegrated and dissolved at the absorption sites and prepared by a simple method by omitting the step of forming a water-soluble inner film.

What is claimed is:

1. An enteric coated formulation of a benzimidazole derivative comprising a core containing a complex of the benzimidazole derivative and an anion-exchange resin, and an enteric coating on the surface of said core, said enteric coating being hydroxypropyl methylcellulose phthalate having a degree of substitution by phthalic acid group of 20 to 27% lansoprazole.

2. A method for preparation of an enteric coated formulation of a benzimidazole derivative, comprising coating a core containing a complex of a benzimidazole derivative and an anion-exchange resin with an entetic coating agent of hydroxypropyl methylcellulose phthalate having a degree of substitution by phthalic acid of 20 to 27% lansoprazole.

* * * * *

UNITED STATES PATENT AND TRADEMARK OFFICE
CERTIFICATE OF CORRECTION

PATENT NO.    : 6,706,285 B1
DATED         : March 16, 2004
INVENTOR(S)   : Jong Soo Woo It is certified that error appears in the above-identified patent and that said Letters Patent is hereby corrected as shown below:

Title page,
Item [73], Assignee, change "Hanms Pharm. Co., Ltd., Kyunggi-do (KR)" to
-- Hanmi Pharm. Co., Ltd., Kyunggi-do (KR) --

Signed and Sealed this

Twenty-second Day of June, 2004

JON W. DUDAS
*Acting Director of the United States Patent and Trademark Office*